United States Patent [19]

Hase et al.

[11] 4,110,242

[45] Aug. 29, 1978

[54] COMPOSITIONS AND METHOD FOR ACTIVATING OXYGEN UTILIZING N-ACYLATED URACILS AND BENZOURACILS

[75] Inventors: Christian Hase; Brigitte Hase, both of Erkrath-Unterbach, Fed. Rep. of Germany

[73] Assignee: Henkel Kommanditgesellschaft auf Aktien, Dusseldorf-Holthausen, Fed. Rep. of Germany

[21] Appl. No.: 782,334

[22] Filed: Mar. 29, 1977

[30] Foreign Application Priority Data

Apr. 2, 1976 [DE] Fed. Rep. of Germany ....... 2614148

[51] Int. Cl.[2] .............................................. A61L 13/00

[52] U.S. Cl. .................................... 252/186; 252/102; 8/107; 423/272; 423/273; 260/45.8 N

[58] Field of Search .................... 252/186, 102; 8/107; 423/272, 273; 260/45.8 N

[56] References Cited

U.S. PATENT DOCUMENTS

| | | | |
|---|---|---|---|
| 3,836,636 | 9/1974 | Kuhling | 252/186 X |
| 3,986,971 | 10/1976 | Loffelman et al. | 252/186 X |

*Primary Examiner*—Stephen J. Lechert, Jr.
*Attorney, Agent, or Firm*—Hammond & Littell

[57] ABSTRACT

The method of activating aqueous solutions of percompounds utilizing N-acylated uracils and benzouracils as activators; solid activated compositions comprising solid percompounds and N-acylated uracils and benzouracils as activators; and novel diacylated uracils and benzouracils.

20 Claims, No Drawings

COMPOSITIONS AND METHOD FOR ACTIVATING OXYGEN UTILIZING N-ACYLATED URACILS AND BENZOURACILS

RELATED ART

It is common knowledge that inorganic peroxides, particularly hydrogen peroxide and peroxide hydrates, such as perborate, percarbonate and perpyrophosphate, develop their full oxidation and bleaching action in aqueous solution only at temperatures in excess of 80° C. In order to obtain an adequate bleaching action even at lower temperatures, it has been proposed to add specific N-acyl compounds to the aqueous solutions of percompounds in order to activate the latter. According to German Published Application DAS No. 1,162,967, the compounds used for this purpose should contain at least two acyl groups attached to the same nitrogen atom, such as N,N,N'-triacetylmethylenediamine, N,N,N',N'-tetraacetylmethylenediamine and the like. According to German Published Application DAS No. 1,291,317, compounds of the general formula $$RCO - NR_2 - OCR_1$$

serve this purpose, wherein R and $R_1$ signify $C_{1-3}$ alkyl residues, while $R_2$ may constitute an optional organic radical which may be combined with $R_1$ to form a ring, if desired substituted, such as caprolactam, N-acylated barbitone, phthalimide, anthranil, N-acylated hydantoin or saccharine rings. U.S. Pat. No. 3,715,184, describes the use of acylated glycolurils of the general formula

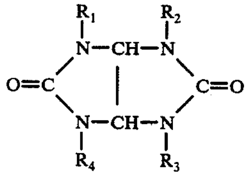

wherein at least two of the residues $R_1$ and $R_4$ constitute acyl residues having 2 to 8 carbon atoms, while the other residues signify hydrogen atoms and/or alkyl or aryl residues having 1 to 8 carbon atoms and/or acyl residues having 2 to 8 carbon atoms, as activators for percompounds. The acyl residues present in one molecule may be the same or different. Preferably, tetraacylglycolurils having similar $C_{2-4}$ acyl residues are used, particularly tetraacetylglycoluril.

Preferred examples of bleaching activators of this type are tetraacetylmethylenediamine, tetraacetylethylenediamine, diacetyl-p-toluidine, diacetylurea and tetraacetylglycoluril. The acylated nitrogen compounds hydrolyze in the presence of aqueous hydrogen peroxide to form peracids which develop a satisfactory bleaching and disinfecting action even in the range of temperature between 30° and 60° C. However, certain difficulties are involved in the storage of washing and bleaching agent mixtures containing percompounds as well as bleaching activators. If special precautionary measures are not taken, increased atmospheric humidity can cause a partial reaction in the powder mixtures between the percompound and the activator, thus leading to a loss of activity and to the destruction of the constituents of the washing agents which are sensitive to oxidation, such as the optical brightening agents. Therefore, it has been proposed to provide the bleaching activators with a protective coating of, for example, film-forming polymers or water-repellent fat-like substances such as fatty acids or fatty alcohols, or to embed the bleaching activators therein. In addition to the fact that an additional working operation is required in order to coat the bleaching activators, the protective action of coatings made from water-soluble polymers is frequently inadequate, while fat-like embedding materials can considerably impair the dissolving rate in cold or moderately warm water. U.S. Pat. No. 3,925,234 describes an improvement in such methods by employing mixtures of fatty acids and fatty alcohols or ethoxylates and spraying the hot mix with activator to give very fine particles with an improved dissolving rate.

It has also been proposed, in German Auslegeschrift (DAS) No. 2,360,340, to use oxamides of the formula $$R - NH - CO - CO - NH - R'$$

in which R and R' represent acyl radicals having 2 to 9 carbon atoms as bleaching activators. These oxamides are said to be distinguished by improved storage stability in the presence of peroxide. However, a substantial disadvantage of the described oxamides is their relatively very low activation value. Thus, in order to obtain adequate activation, very large quantities of bleaching activators have to be used, only a slight cold-bleaching action being obtainable when using quantities which meet practical requirements.

Therefore, the task arose of providing new oxidation, bleaching and washing agents having a content of bleaching activators which do not have the aforementioned disadvantages.

OBJECTS OF THE INVENTION

An object of the present invention is to develop solid compositions with bleaches and bleach activators which have improved storage stability when employed in conventional quantities.

Another object of the present invention is the development of solid oxidation compositions for washing and bleaching agents containing compounds releasing active oxygen in solution and at least one N-acylated uracil or benzouracil.

A yet further object of the present invention is the development of a method of activating aqueous solutions of percompounds at temperatures below 70° C. by utilization of at least one N-acylated uracil or benzouracil.

A still further object of the present invention is the obtaining of novel diacylated uracils or benzouracils useful as bleach activators.

These and other objects of the present invention will become more apparent as the description thereof proceeds.

DESCRIPTION OF THE INVENTION

Accordingly the present invention provides oxidation, bleaching and washing agents comprising inorganic percompounds and acylated uracils of the formula

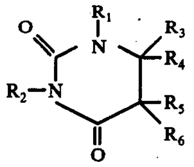

in which one of the radicals $R_1$ and $R_2$ represents an acyl of an organic carboxylic acid having 2 to 10 carbon atoms, preferably an acetyl, propionyl, or benzoyl group and the other one of the radicals $R_1$ and $R_2$ represents an acyl, such as acetyl, propionyl or benzoyl, hydrogen or an optionally substituted alkyl group having 1 to 4 carbon atoms, and the radicals $R_3$, $R_4$, $R_5$ or $R_6$ represent, independently of one another, hydrogen, alkyl groups having 1 to 4 carbon atoms, which can be optionally substituted by halogens, alkoxy, carboxyl or carboxylic ester groups, or represent members of an optionally substituted benzene ring.

More particularly, the bleach activator is an acylated uracil of the formula selected from the group consisting of

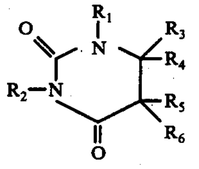

and

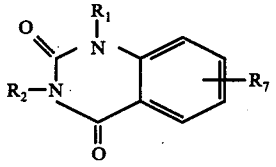

wherein at least one of $R_1$ and $R_2$ is an acyl of an acid selected from the group consisting of alkanoic acids having 2 to 4 carbon atoms and benzoic acid, and the other of $R_1$ or $R_2$ is a member selected from the group consisting of alkanoyl having 2 to 4 carbon atoms, benzoyl, and $R_3$; $R_3$, $R_4$, $R_5$ and $R_6$ are independently members selected from the group consisting of hydrogen, alkyl having 1 to 4 carbon atoms, haloalkyl having 1 to 4 carbon atoms, alkoxyalkyl having 2 to 6 carbon atoms, carboxyalkyl having 2 to 4 carbon atoms, and alkoxycarbalkyl having 3 to 6 carbon atoms, and $R_7$ is a member selected from the group consisting of hydrogen, halogen, alkyl having 1 to 4 carbon atoms, $—CO_2Me$, $—SO_3Me$, amido, cyano, sulfamido and nitro, where Me is an alkali metal or ammonium.

Suitable compounds, in which the radicals $R_3$ to $R_6$ do not represent ring member, are, for example:

1-acetyl-5,6-dihydrouracil
1-propionyl-5,6-dihydrouracil
1-benzoyl-5,6-dihydrouracil
1,3-diacetyl-5,6-dihydrouracil
1,3-dipropionyl-5,6-dihydrouracil
1,3-dibenzoyl-5,6-dihydrouracil
1-acetyl-3-propionyl-5,6-dihydrouracil
1-acetyl-3-methyl-5,6-dihydrouracil
1-methyl-3-acetyl-5,6-dihydrouracil
1-acetyl-5-methyl-5,6-dihydrouracil
1,3-diacetyl-5-methyl-5,6-dihydrouracil
1-acetyl-6-methyl-5,6-dihydrouracil
1,3-diacetyl-6-methyl-5,6-dihydrouracil
1,3-dipropionyl-5-methyl-5,6-dihydrouracil
1,3-dipropionyl-6-methyl-5,6-dihydrouracil
1,3-diacetyl-5-chloromethyl-5,6-dihydrouracil
1,3-diacetyl-6-chloromethyl-5,6-dihydrouracil
1,3-diacetyl-5-(β-methoxyethyl)-5,6-dihydrouracil
1,3-diacetyl-6-(β-methoxyethyl)-5,6-dihydrouracil
1-acetyl-3-(β-methoxyethyl)-5,6-dihydrouracil, and
1-(β-methoxyethyl)-3-acetyl-5,6-dihydrouracil.

Examples of acylated uracils, in which the radicals $R_3$, $R_4$, $R_5$ and $R_6$ represent members of a ring system of the following formula

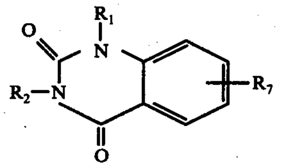

in which $R_7$ represents H, Cl, $C_1$ to $C_4$ alkyl groups, $CO_2Me$, $SO_3Me$, $CONH_2$, CN, $SO_2NH_2$ or $NO_2$, and Me represents Na, K or $NH_4$, are:

1-acetyl-5,6-benzouracil
1,3-diacetylbenzouracil
1-acetyl-3-methylbenzouracil
1-methyl-3-acetylbenzouracil
1,3-dipropionylbenzouracil
1,3-dibenzoylbenzouracil, and
1,3-diacetylbenzouracils, which carry in the 5-, 6-, 7- or 8-position on the benzene group one of the radicals designated $R_7$.

Preferably, acylated uracils are used such as 1-acetyl-5,6-dihydrouracil and those having two acetyl groups, such as 1,3-diacetyl-5,6-dihydrouracil. Diacylated 5,6-dihydrouracils and benzouracils are novel substances and, as such, are also the subject of the present invention.

The 5,6-dihydrouracils or benzouracils can be acylated in a known manner by, for example, reaction with acid anhydrides, acid chlorides or acid bromides or with ketenes. It is advantageous to use a surplus of acid anhydrides, such as 2 to 10 mols of acid anhydride relative to 1 mol of the uracil derivative. Advantageously, acylation with acid anhydrides is effected at an increased temperature, for example, at 50° to 118° C. The acylation can be accelerated by adding small quantities of acylation catalysts, particularly strong mineral acids, such as concentrated sulfuric acid or perchloric acid. The reaction is completed in from 1 to 10 hours according to the excess quantity of acylation agent and the reaction temperature. Reaction with acid anhydrides generally leads to monoacylated compounds, and reaction with ketenes, particularly with that of formula $CH_2=C=O$, leads to diacylated compounds.

Furthermore, the present invention relates to the use of the above-described acylated uracils as activators for $H_2O_2$ or percompounds producing $H_2O_2$ in water.

The percompounds to be activated in aqueous solution can be any type of inorganic or organic percompound which will release active oxygen in an aqueous solution. For economic reasons, the percompounds preferably utilized are inorganic peroxides, inorganic peracids, inorganic peroxyhydrates and products of the addition of hydrogen peroxide with inorganic and organic compounds.

Of the peroxides to be activated, hydrogen peroxide is of the greatest practical importance. It may be used as such, but may also be used in the form of its mostly solid peroxyhydrates or products of addition with inorganic and organic compounds. The latter include, for example, the products of addition of hydrogen peroxide to urea or melamine, and examples of the peroxyhydrates are the perborates, perortho-, perpyro-, and perpolyphosphates, percarbonates and persilicates. These peroxyhydrates are preferably soluble in water and are ordinarily utilized in the form of their alkali metal salts, such as their sodium salts. The activators, according to the invention, however, may also be used together with true peracids, such as, for example, Caro's acid (peroxymonosulfuric acid, $H_2SO_5$) or peroxydisulfuric acid ($H_2S_2O_8$) or their salts.

Each acyl residue present in the acetylated uracil activator is able to activate an active oxygen atom of the percompound used. Therefore, in theory, the activator and percompound should be used in equivalent amounts for complete activation of the active oxygen present. In practice, however, satisfactory effects are attained in many cases even with substantially smaller amounts of activator, while on the other hand, the activator may also be used in relatively large excess.

The activation, in accordance with the invention, of the oxygen is most clearly perceptible at temperatures in the range of 20° to 70° C., especially from 30° to 60° C. Nevertheless, it is possible to use higher temperatures up to 100° C., for example, particularly when using deficient quantities of activator, so that chemically activated oxygen is used at temperatures up to 70° C. and thermally activated oxygen at higher temperatures, particularly temperatures in excess of 80° C. Depending upon the problem to be solved, it is possible for the technician, when using the activators according to the invention, either to reduce the temperature of treatment and/or to shorten the time of treatment, the temperature remaining the same.

Finally, a low and a high temperature bleach can also be combined in one operation. In such cases, it may be advantageous to add less than the theoretical amounts of activator, then at low temperatures only a part of the active oxygen present is activated, and the remainder is available for the bleaching at elevated temperatures.

The conditions to be maintained during operation with the activators according to the invention, such as, for example, the concentration of the peroxide, temperature, pH value and time of treatment, depend substantially on the substance to be oxidized and/or bleached, and in some cases on the carrier material on or in which the substance to be bleached is present. The usually aqueous oxidizing or bleaching liquids may contain from 20 mg to 500 mg, preferably from 50 mg to 250 mg, per liter of active oxygen and have a pH value of from 4 to 12, preferably from 7 to 11.5, and particularly from 8 to 11. It should be kept in mind that the activators act by way of the intermediately formed percarboxylic acids. Therefore, carboxylic acid is produced during the oxidation or bleaching process and this should be neutralized by an alkali if a shift in the pH value is not desired.

As indicated, aqueous solutions of percompounds and the N-acylated uracils, optionally with other ingredients, as indicated below, may be utilized. These aqueous solutions preferably contain sufficient percompounds to give a concentration of from 20 mg to 500 mg, preferably 50 mg to 250 mg per liter of active oxygen and sufficient N-acylated uracil activator to provide from 0.05 to 5, preferably 0.1 to 2 acyls of the N-acylated activator per active oxygen atom.

The activators according to the invention may be used whereever percompounds, especially hydrogen peroxide or perborates, have previously been used as oxidizing and/or bleaching agents. This applies, for example, to the bleaching oils, fats and waxes, to cosmetic skin and hair treatment, in disinfection or sterilization, in passivation of aluminum or other light metal surfaces, and especially in the bleaching of fibrous substances of all kinds.

The acylated uracils can be added to the oxidation, bleaching and cleaning agents or solutions immediately before use or, alternatively, they can be incorporated in the pulverulent or granular washing and bleaching agents and used together therewith. In addition to inorganic percompounds, such as sodium perborate or urea perhydrate, such washing and bleaching agents can contain further conventional washing-active substances, such as surface-active compounds or tensides, wash alkalis, sequestering agents which bind calcium salts, and other builders as well as further additives conventionally contained in washing and cleaning agents.

Advantageously, the compounded agents contain the acylated uracils and the percompounds in the ratio of 0.5 to 10, preferably 1 to 5, mols of peroxygen to 1 mol of monoacylated uracil, and 1 to 20, preferably 2 to 10, mols of peroxygen to 1 mol of diacylated uracil. Furthermore, the joint use of alkaline reacting compounds, such as the alkali metal carbonates, bicarbonates, borates, silicates and phosphates or condensed alkali metal phosphates, is advisable in quantities such that the carboxylic acid, released during the bleaching process, is fully or at least partially neutralized.

Suitable surface-active compounds or tensides are those of the sulfonate or sulfate type, such as alkylbenzene sulfonates, particularly n-dodecylbenzene sulfonate, olefinsulfonates, alkylsulfonates and α-sulfo-fatty acid esters, primary and secondary alkyl sulfates, as well as the sulfates of ethoxylated or propoxylated fatty alcohols. The sulfated partial ethers and partial esters of polyhydric alcohols are also usable, such as the alkali salts of mono-higher-alkyl ether or of mono-higher-fatty acid ester of glycerol-monosulfuric acid ester or of 1,2-dioxypropane sulfonic acid. Sulfates of ethoxylated or propoxylated fatty acid amides and alkylphenols, as well as fatty acid taurides and fatty acid isothionates are also suitable.

Further suitable anionic surface-active compounds are alkali metal soaps of higher fatty acids of natural or synthetic origin, such as sodium soaps of coconut fatty acids, palm kernel fatty acids, or tallow fatty acids. Suitable zwitterionic surface-active compounds are the alkylbetaines and particularly alkylsulfobetaines, such as 3-(N,N-dimethyl-N-higher-alkylammonium)-propane-1-sulfonate and 3-(N,N-dimethyl-N-higher-alkylammonium)-2-hydroxypropane-1-sulfonate.

The anionic surface-active compound may be present in the form of their alkali metal salts, such as sodium or potassium, and ammonium salts as well as salts of organic bases, such as mono-, di- or triethanolamine. Insofar as the said anionic and zwitterionic surface-active compounds have an aliphatic hydrocarbon radical, the latter should be preferably straight chain and have 8 to 22 carbon atoms. In the compounds having an araliphatic hydrocarbon radical, the preferably unbranched alkyl chains contain an average of 6 to 16 carbon atoms. The aryl hydrocarbon radical is cyclohexyl or preferably phenyl.

Suitable nonionic surface-active compounds or tensides are those of the class of the polyglycolether derivatives, such as those of alcohols having 10 to 24 carbon atoms from the group of alkanols, alkenols and alkanediols and/or alkylphenols having 6 to 15 carbon atoms in the alkyl chain and 3 to 30 alkoxy units. The alkoxy units are propoxy or preferably ethoxy and mixtures of propoxy and ethoxy units. Mixtures of such polyglycolether derivatives are particularly suitable in which at least one compound having 3 to 6 ethoxy units and at least one compound having 7 to 20 ethoxy units are present in the weight ratio of 5:1 to 1:10. Preferably polyglycolether derivatives of straight chain, primary alkanols having 12 to 18 carbon atoms, and of alkylphenols having straight chain alkyl chains having 8 to 12 carbon atoms, are used.

Further suitable nonionic surface-active compounds are the glycolether derivatives of higher fatty acids, higher fatty acid amides, primary or secondary higher fatty amines, vacinal higher alkane diols, higher alkyl mercaptans and alkyl sulfamides which have 10 to 24 carbon atoms in the hydrocarbon radical and 3 to 30 glycolether groups, preferably ethoxy units. Nonionic surface-active compounds of the type of aminoxides and sulfoxides, which may be optionally ethoxylated, are also usable.

Suitable builders are the alkali metal carbonates and silicates, such as potassium and particularly of sodium, the latter having a ratio of $SiO_2$ to $Na_2O$ of 1:1 to 3.5:1. Suitable builders having a sequestering action are polymeric phosphates, particularly pentasodium tripolyphosphate which may be present mixed with its products of hydrolysis, the mono- and diphosphates, as well as higher condensed phosphates such as tetrapolyphosphates.

Alternatively, the polymeric phosphates can be entirely or partially replaced by phosphate-free sequestering agents. These include the alkali metal salts of aminopolycarboxylic acids, particularly nitrilotriacetic acid and ethylenediaminotetraacetic acid. Also suitable are the salts of diethylenetriaminopentaacetic acid as well as the higher homologues of the said aminopolycarboxylic acids. Further suitable aminopolycarboxylic acids, are poly-(N-succinic acid)-ethylene imine, poly-(N-tricarballylic acid)-ethylene imine and poly-(N-butane-2,3,4-tricarboxylic acid)-ethylene imine.

The salts of aminopolycarboxylic acids can be replaced by, or mixed with, polyphosphonic acids having a sequestering action, such as alkali metal salts of aminopolyphosphonic acids, particularly amino-tri-(methylene phosphonic acid), 1-hydroxyethane-1,1-diphosphonic acid, methylene diphosphonic acid, ethylene diphosphonic acid as well as salts of the higher homologues of the said polyphosphonic acids.

Particular importance is attached to the nitrogen and phosphorus-free polycarboxylic acids forming complex salts with calcium ions, including polymers containing carboxyl groups. Citric acid, tartaric acid, benzenehexacarboxylic acid and tetrahydrofurantetracarboxylic acid are also suitable. Polycarboxylic acids containing carboxy methyl ether groups are also usable, such as 2,2′-oxydisuccinic acid as well as polyvalent alcohols or hydroxycarboxylic acids partially or fully etherified with glycolic acid, such as triscarboxymethyl glycerine, biscarboxymethyl glyceric acid an carboxymethylated or oxygenated poly saccharides. Also suitable are the polymeric carboxylic acids having a molecular weight of at least 350 in the form of water-soluble sodium or potassium salts, such as polyacrylic acid, polymethacrylic acid, poly $\alpha$-hydroxyacrylic acid, polymaleic acid, polyitaconic acid, polymesaconic acid, polybutenetricarboxylic acid, as well as the copolymers of the corresponding monomeric carboxylic acids one with another or with ethylenically-unsaturated compounds such as ethylene, propylene, isobutylene, vinylmethyl ether or furan.

Water-insoluble complex formers may also be used. These include phosphorylated cellulose and graft polymers of acrylic acid or methacrylic acid on cellulose, which can be present in the form of textile fabric, nonwoven fabric or powder. Also suitable are spatially cross-linked and thus water-insoluble copolymers of acrylic acid, methacrylic acid, crotonic acid and maleic acid as other polymerizable polycarboxylic acids optionally with further ethylenically-unsaturated compounds in the form of sodium or potassium salts as sequestering agents. These insoluble copolymers can be in the form of fleeces, sponges, or alternatively, in the form of finely-ground foams having a low specific gravity and an open-cell structure.

Further suitable water-insoluble builders having a sequestering capability are alkali metal amuminosilicates which optionally contain bound water and in which the alkali metal can be exchanged for calcium or magnesium. These substances include, particularly, finely crystalline-to-amorphous aluminosilicates of the formula $$(Na_2O)_x . Al_2O_3 . (SiO_2)_y$$

wherein $x$ represents a number of from 0.7 to 1.5, and y represents a number of from 1.3 to 4. The use of these aluminosilicates as builders is described in copending U.S. patent application Ser. No. 458,306, filed Apr. 5, 1974. Alternatively, mixtures of the aforesaid water-soluble and water-insoluble builders or complex formers can be used.

Magnesium silicate is particularly suitable as a stabilizer for the percompounds. Furthermore, enzymes from the class of the proteases, amylases and lipases may be present, particularly bacterial enzymes, such as those obtained from Bacillus subtilis.

Furthermore, the washing agents can contain optical brighteners, particularly derivatives of diaminostilbene disulfonic acids or their alkali metal salts. Salts of 4,4′-bis(2″-anilino-4″-morpholino-1,3,5-triazinyl-6″-amino)-stilbene-2,2′-disulfonic acid, for example, are suitable or similar compounds which contain, instead of the morpholino group, a diethanolamino group, a methylamino group, or a $\beta$-methoxyethylamino group. Furthermore, suitable optical brighteners for polyamide fibers are those of the diarylpyrazoline type, such as 1-(p-sulfonamidophenyl)3-(p-chlorophenyl-$\Delta^2$-pyrazoline, as well as similar compounds which contain a carboxymethyl or acetylamino group instead of the sulfonamido group. Furthermore, substituted aminocumarins are usable, such as 4-methyl-7-dimethyl-amino-cumarin or 4-methyl-7-diethylamino-cumarin.

In addition, the compounds 1-(2-benzimidazolyl)-2-(1-hydroxyethyl-2-benzimidazolyl)-ethylene and 1-ethyl-3-phenyl-7-diethylamino-carbostyril and usable as polyamide brighteners. Suitable optical brighteners for polyester and polyamide fibers are the compounds 2,5-di-(2-benzoxazolyl)thiophene, 2-(2-benzoxazolyl)-naphtho-[2,3-b]-thiophene and 1,2-di-(5-methyl-2-benzoxazolyl)-ethylene. Furthermore, optical brighteners of the substituted diphenylstyril type may be present. Mixtures of the aforesaid optical brighteners may also be used.

Particularly suitable greying inhibitors or soil suspension agents are carboxymethylcellulose, methylcellulose, water-soluble polyesters and polyamides from polyvalent carboxylic acids and glycols or diamines which have free carboxyl groups, betaine groups or sulfobetaine groups capable of forming salts, as well as polymers or copolymers which are colloidally soluble in water, of vinyl alcohol, vinyl pyrrolidone, acrylamide and acrylonitrile.

Further suitable constituents neutral salts, particularly sodium sulfate, as well as biocides or antimicrobials, such as halogenated diphenylmethanes, salicylanilides, carbanilides and phenols. Furthermore, liquid agents can contain hydrotropic substances and solvents, such as alkali metal salts of benzene sulfonic acid, toluene sulfonic acid or xylene sulfonic acid, urea, glycerine, polyglycerine, diethyleneglycol, or triethyleneglycol, polyethyleneglycol, ethanol, i-propanol, and other ether alcohols.

If required, known foam stabilizers, such as fatty acid alkanolamides, may also be present, such as laurylmonoethanolamide or diethanolamide or coconut fatty acid mono- or diisopropanolamides.

The acrylated uracils to be used in accordance with the invention may be mixed with the pulverulent bleaching and washing agents, containing inorganic percompounds, without special precautions, since, even without a protective coating, they have adequate storage stability when stored under normal conditions. It is only in those cases in which it is impossible to avoid longer storage times at temperatures in excess of 25° to 30° C and high relative atmospheric humidity that it may be advisable to store the bleaching activators separately from the washing and bleaching agents containing persalt or to provide them with a protective coating of water-repellent materials or to embed them therein.

Examples of such cases of application are tablets which contain, in addition to the bleaching activator, conventional tabletting agents, such as starch, starch ether, microcrystalline or depolymerized cellulose, cellulose ether or swellable magnesium aluminum silicates ("Veegum", registered trademark), and alkali earth metal soaps, particularly magnesium stearate, as well as finely powdered mineral parting agents, particularly colloidal $SiO_2$ ("Aerosil", registered trademark) and, if required, surface-active wetting agents which promote the wetting and dissolving capacity. It will be appreciated that, alternatively, tablets of this type may be composed such that they contain the bleaching activator as well as the inorganic percompound (both of them preferably in a pregranulated form) and, optionally, further constituents of washing agents. In this case, the tabletting agent at the same time acts as a parting agent between the reactants.

A further embodiment suitable for particularly unfavorable storage conditions is the embedding of the bleaching activators in so-called "prills", i.e., loose powders which are producible by spraying a molten mass with simultaneous cooling of the material sprayed and which substantially comprise spherical individual particles having a diameter of approximately 0.1 to 2.5 mm. Embedding materials which have proved to be successful are, in particular, mixtures of insoluble fat-like compounds, particularly fatty acid mixtures and/or fatty alcohols melting between 35° and 60° C, as well as water-soluble, plasticizable compounds such as polyethyleneglycols and/or polyethyleneglycol ethers of fatty alcohols, alkylphenols, fatty acids, fatty acid amides, diols and other water-soluble polyglycol ether derivatives. By way of example, the weight ratio of water-insoluble to water-soluble embedding components can be 5:1 to 1:1. In addition, it is also possible to incorporate cellulose or starch ethers or "disintegrating agents" having a similar action and which are swellable in water and promote the dissolving capacity. The prills can be directly incorporated in the pulverulent oxidation, bleaching and washing agents. Such embedding processes are described in U.S. Pat. No. 4,003,841.

The acylated uracils can also be used to advantage in polishing and scouring agents. In addition to the inorganic peroxides and, if required, tensides and builders, these polishing and scouring agents can also contain abrasives such as pumice powder, marble powder, feldspar or quartz powder, corundum, synthetic resin granulates, steel cuttings or mixtures of such abrasives. The polishing and scouring agents may be present in the form of powder, rods or cubes or, alternatively, in a liquid form or in polishing pads based on steel wool or plastic wool which are impregnated with effective cleaning and bleaching substances.

Further fields of application for the acylated uracils and mixtures thereof with organic peroxides are washing agents for automatic dishwashers, disinfectants and deodorizing preparations for the sanitary and clinical field where they may be used in, for example, toilet and and drain cleaners, for disinfecting swimming pools and for the sterilizing or medical instruments and infected articles, as well as the food and beverage industry, for example, as an additive to alkaline cleaners for bottles and milk cans and in so-called beer coils, for sterilizing the water used for washing beer glasses in restaurants. They are also suitable for disinfecting the body and for the bleaching of human hair or, alternatively, for brightening chemical compounds. Basically, it is possible to use them in all fields in which agents containing active chlorine are customarily used and in which the aggressive properties and the unpleasant odor of chlorine are troublesome.

The special advantage of the acylated uracils compared with other polyacylated amines or amides proposed as bleaching activators resides in the fact that the ratio of mols of reactive acyl group to mols of acylation product used is particularly high in the compounds to be used in accordance with the invention. While all the acyl groups are available for the formation of peracid in the case of the acylated uracils, only approximately half of all the acyl groups are capable of forming peracid in the case of, for example, tetraacetylglycoluril or tetraacetylethylenediamine as typical representatives of the known bleaching activators. Thus, smaller quantities of bleaching activators are required to obtain the same bleaching effect in the case of the agents in accordance with the invention.

The oxidation, bleaching and washing agents generally contain the acylated uracils in quantities of from 0.5% to 50%, preferably from 1% to 30% by weight. Some basic formulations for bleaching, washing and cleaning agents in which the acylated uracils have proved to be successful, are given hereinafter. However, the range of application is not confined to these formulations.

FORMULATIONS

A. Washing Agent

5% to 40%, preferably 12% to 30%, by weight of tensides or combinations of tensides, comprising:
- 0 to 100%, preferably 25% to 65%, by weight of anionic tensides of the sulfonate and/or sulfate type,
- 1% to 100%, preferably 5% to 40%, by weight of nonionic tensides,
- 0 to 100%, preferably 10% to 50%, by weight of soap,
- 0 to 6%, preferably 0.5% to 3%, by weight of foam stabilizer,
- 0 to 8%, preferably 0.5% to 5%, by weight of foam inhibitor, 10% to 82%, preferably 35% to 75%, by weight of builders wherein at least a portion of these builders react alkaline, and wherein the amount of the alkaline to neutral reacting builders amounts preferably to 0.5-fold to 7-fold, and particularly 1-fold to 5-fold the total tenside component, 10% to 50%, preferably 15% to 35%, by weight of a combination of percompound, particularly perborate and acylated uracils and, if required, stabilizers for the percompound, the quantity of this combination preferably being such that the active oxygen content of the total bleaching and washing agent amounts to 1% to 4%, preferably 1.5% to 3.5% by weight.

0 to 15%, preferably 1% to 12%, by weight of other washing agent constituents, such as soil suspension agents, optical brighteners, enzymes, perfume, dyes, and water.

B. Scouring Agent

60% to 95%, preferably 80% to 90%, by weight of water-insoluble constituents having a scouring action.

40% to 5%, preferably 20% to 10%, by weight of an essentially water-soluble mixture comprising:
- 5% to 100%, preferably 10% to 50%, by weight of a combination of percompound and acylated uracils, the quantity ratio of percompound to activator lying in the range given above,
- 0 to 95%, preferably 10% to 60%, by weight of anionic, nonionic and/or zwitter-ionic tensides,
- 0 to 95%, preferably 10% to 50%, by weight of particularly alkaline reacting inorganic builders and organic complex formers,
- 0 to 20%, preferably 1 to 10%, by weight of other conventional constituents of scouring agents.

C. AGENT FOR DISHWASHING MACHINES 0 to 5%, preferably 0.1% to 3%, by weight of a low-foaming tenside, particularly a nonionic surface-active compound from the class of the block polymers of ethylene oxide and peropylene oxide, 30% to 98%, preferably 40% to 95%, by weight of builders, wherein at least a portion of these builders reacts alkaline and is preferably composed of the following:

- 20% to 100% by weight of Na or K tripolyphosphate,
- 0 to 90% by weight of a water-insoluble, cation-exchanging sodium aluminosilicate,
- 0 to 50%, preferably 5% to 50%, by weight of sodium silicate ($Na_2O : SiO_2 = 1:1$ to $1:3.5$), 0.1% to 50%, preferably 0.5% to 10%, by weight of a combination comprising an inorganic percompound, particularly perborate and acylated uracils and, if required, stabilizers for the percompound, the quantity ratio of activator to percompound corresponding to the range given above.

D. Alkaline Cleaner

50% to 99% by weight of at least one alkaline-reacting compound from the class of the sodium or potassium hydroxides, carbonates, phosphates, polymeric phosphates, borates and silicates ($Na_2O : SiO_2 = 2:1$ to $1:3$), 0 to 20%, preferably 0.1% to 10%, by weight of at least one sequestering agent from the class of the aminopolyphosphonates and hydroxyalkanepolyphosphonates, 0 to 5%, preferably 0.1% to 3%, by weight of at least one nonionic and/or anionic surfactant, 0.1% to 20%, preferably 0.2% to 10% by weight of a combination of inorganic percompound, particularly perborate, and acylated uracils and, if required, stabilizers for the percompound, the quantity ratio of activator to percompound corresponding to the range given above.

E. Bleaching Agent

10% to 100%, preferably 50% to 95%, by weight of a combination of inorganic percompound, particularly perborate and acylated uracils and, if required, stabilizers for the percompound, the quantity ratio of activator to percompound corresponding to the range given above, 0 to 50%, preferably 2% to 25%, by weight of at least one alkaline-reacting compound from the class of the sodium or potassium hydroxides, carbonates, phosphates, polymeric phosphates, borates and silicates ($Na_2O : SiO_2 = 2:1$ to $1:3$), 0 to 20%, preferably 0.1% to 10%, by weight of at least one sequestering agent from the class of the aminopolycarboxylates, aminopolyphosphonates and hydroxyalkanepolyphosphonates, 0 to 20%, preferably 0.1% to 10%, by weight of other constituents, such as corrosion inhibitors, optical brighteners and neutral salts.

Sodium perborate tetrahydrate (NaBO2 . $H_2O_2$ . $3H_2O$) has particular practical importance among the preferably inorganic percompounds yielding $H_2O_2$ in aqueous solution. Partially or completely dehydrated perborates, i.e., perborates dehydrated up to $NaBO_2$ . $H_2O_2$, may be used instead of sodium perborate tetrahydrate. Alternatively, the borates $NaBO_2 . H_2O_2$ (as described in German Pat. No. 901,287 or in U.S. Pat. No. 2,491,789) may be used in which the ratio $Na_2O : B_2O_3$ is less than 0.5:1 and preferably from 0.4 to 0.15:1, while the ratio $H_2O_2$ : Na is from 0.5 to 4:1. All these perborates may be replaced entirely or partially by other inorganic percompounds, particularly by peroxyhydrates, for example, the peroxyhydrates of the ortho-, pyro- or polyphosphates, particularly tripolyphosphates, and of the carbonates. These peroxyhydrates are preferably soluble in water and are ordinarily utilized in the form of their alkali metal salts, such as the sodium salts.

It is advisable to incorporate quantities of form 0.25% to 10% by weight or conventional water-soluble and/or water-insoluble stabilizers for stabilizing the percompounds in the products of the invention. The magnesium silicates of a ratio of $MgO:SiO_2 = 4:1$ to 1:4, preferably 2:1 to 1:2, and particularly 1:1, generally obtained by precipitation from aqueous solutions, are suitable as water-insoluble stabilizers for percompounds. These compounds, for example, amount to from 1% to 8%, preferably 2% to 7%, of the weight of the entire preparation. Other alkaline earth metal silicates, cadmium silicates or tin silicates of corresponding composition may be used instead of the magnesium silicates. Water-containing oxides of tin are also suitable as stabilizers. Stabilizers soluble in water, which may be present together with stabilizers insoluble in water, are the organic complex formers whose quantity can amount to 0.25% to 5%, preferably 0.5% to 2.5%, of the weight of the entire preparation.

The following examples are illustrative of the practice of the invention without being limitative in any respect.

EXAMPLES

(1) Production of the Acylated Uracils

I. 1-acetyl-5,6-dihydrouracil 57 gm (0.5 mol) of 5,6-dihydrouracil and 817 gm (8 mols) of acetic acid anhydride were heated to boiling for ten hours after adding 2 ml of concentrated sulfuric acid thereto. The acetic acid produced was continuously distilled off by means of a fractionating column. After the acylation reaction had been completed, the surplus acetic acid anhydride was distilled off in vacuo (15 Torr) and the residue was recrystallized from isopropanol. The product obtained had a melting point of 191° to 193° C, and the elementary analysis resulted in the following values:

Calculated: C 46.2% : H 5.13% : N 17.9%. Found: 46.1 : 5.20 : 18.1.

II. 1-acetyl-5-methyl-5,6-dihydrouracil

In the manner described in I, 65 gm (0.5 mol) of 5-methyl-5,6-dihydrouracil and 817 gm (8 mols) of acetic acid anhydride and 2 ml of concentrated sulfuric acid were heated to boiling for ten hours with continuous distilling off of the acetic acid produced. The product, isolated after separating of the surplus acetic acid anhydride and purified by recrystallization from isopropanol, had a melting point of 111° C to 113° C. The analysis values were as follows:

Calculated: C 49.4% : H 5.92% : N 16.5%. Found: 49.3 : 5.93 : 16.6.

III. 1-acetyl-6-methyl-5,6-dihydrouracil

In the manner described above, 65 gm (0.5 mol) of 6-methyl-5,6-dihydrouracil were reacted with 8 mols of acetic acid anhydride in the presence of 2 ml of $H_2SO_4$. The product recrystallized from isopropanol had a melting point of 107° C to 109° C and the following analysis values:

Calculated: C 49.4% : H 5.92% : N 16.5%. Found: 49.3 : 5.90 : 16.5.

IV. 1,3-diacetyl-5,6-dihydrouracil

After adding 1.5 gm of finely pulverized sodium acetate suspended in 1 liter of ethyl acetate, 15 gm (0.13 mol) of 5,6-dihydrouracil were reacted with ketene at boiling temperature (77° C). After the reaction had been completed, the catalyst was filtered off and the solvent was distilled off under reduced pressure. The residue was recrystallized from isopropanol. The melting point was 81.5° C to 83° C, and the elementary analysis resulted in the following values:

Calculated: C 48.5% : H 5.09% : N 14.1%. Found: 48.7 : 4.91 : 15.0.

V. 1,3-diacetyl-5-methyl-5,6-dihydrouracil

As described in IV, 18.2 gm (0.14 mol) of 5-methyl-5,6-dihydrouracil were reacted with ketene in boiling ethyl acetate in the presence of sodium acetate. The product recrystallized from isopropanol had the following analysis values and a melting point of 130° C to 131° C:

Calculated: C 50.9% : H 5.66% : N 13.2%. Found: 51.0 : 5.58 : 13.4.

VI. 1,3-diacetyl-6-methyl-5,6-dihydrouracil

In the manner described in IV above, 16.9 gm (0.13 mol) of 6-methyl-5,6-dihydrouracil were reacted with ketene in boiling ethyl acetate in the presence of sodium acetate. The product was recrystallized from a mixture of benzine (b.p. 70° C. to 95° C.) and isopropanol in the volume ratio of 1:1. The melting point was 84° C. to 86° C., and the elementary analysis resulted in the following values:

Calculated: C 50.9%; H 5.66%; N 13.2%. Found: 51.1; 5.52; 14.0.

VII. 1,3-diacetyl-5,6-benzouracil

IV above was repeated with the use of 16.2 gm (0.1 mol) of benzouracil as the starting compound. The analysis values of the product recrystallized from isopropanol were:

Melting point: 142° C. to 145° C. Calculated: C 58.5%; H 4.07%; N 11.4%. Found: 58.7; 4.00; 11.7.

(2) Test of Technical Activity

The N-acyl group reacted in the presence of $H_2O_2$ to form peracetic acid in accordance with the following reaction equation $$>N-CO-CH_3 + H_2O_2 \rightarrow >NH + CH_3CO_3H$$

Thus, a comparison of various N-acetyl compounds for their efficacy is only significant when they are used in quantities which are equivalent relative to the acetyl groups contained. For this reason, 4 m mol of a monoacetyl compound, 2 m mol of a diacetyl compound and 1 m mol of a tetraacetyl compound (tetraacetylglycoluril) were used to activate 4 m mol of $H_2O_2$ in the peracid comparison tests.

For the purpose of carrying out the tests, 2.5 gm of $Na_2P_2O_7 . 10\ H_2O$ and 630 gm of $NaBO_3 . 4\ H_2O$ (4 mg atom active oxygen) were dissolved in $H_2O$ and made up to 1 liter and heated in a thermostat regulated bath to the required test temperature. After adding the corresponding quantity of activator, the mixture was agitated for one hour and the peracid content was determined in dependence upon time. For this purpose, 100 ml of the solution was removed in each case and transferred into a mixture comprising 250 gm of ice and 15 ml of acetic acid. 5 ml of 10% KI solution were subsequently added and the mixture was immediately titrated with 0.1 N sodium thiosulfate solution with a starch solution acting as an indicator. The total content of active oxygen in the perborate solutions used (blank value) was determined manganometrically. If this blank value is set at 100%, the percentage proportion of the active oxygen converted to peracid results from the $Na_2S_2O_3$ titers. These values are listed in the following Tables.

TABLE I

| Time | Test at 30° C | | | | | | | |
|---|---|---|---|---|---|---|---|---|
| | Acylated Uracils | | | | | | | Tetraacetyl- |
| Min. | I | II | III | IV | V | VI | VII | glycoluril |
| 1 | 45 | 54 | 48 | 53 | 81 | 66 | 2 | 45 |
| 5 | 77 | 69 | 86 | 68 | 92 | 80 | 6 | 56 |
| 10 | 87 | 75 | 90 | 72 | 91 | 84 | 12 | 59 |
| 15 | 91 | 82 | 91 | 79 | 90 | 86 | 18 | 61 |
| 30 | 91 | 88 | 93 | 89 | 88 | 90 | 33 | 61 |
| 60 | 90 | 87 | 91 | 88 | 87 | 92 | 54 | 58 |

TABLE II

| Time | Test at 60° C | | | | | | | |
|---|---|---|---|---|---|---|---|---|
| | Acylated Uracils | | | | | | | Tetraacetyl- |
| Min. | I | II | III | IV | V | VI | VII | glycoluril |
| 1 | 78 | 75 | 72 | 72 | 77 | 74 | 8 | 57 |
| 5 | 75 | 80 | 76 | 79 | 70 | 74 | 32 | 57 |
| 10 | 62 | 75 | 68 | 74 | 58 | 66 | 43 | 52 |
| 15 | 54 | 60 | 61 | 62 | 47 | 59 | 45 | 46 |
| 30 | 30 | 38 | 42 | 39 | 26 | 42 | 37 | 33 |
| 60 | 8 | 15 | 19 | 15 | 6 | 22 | 18 | 16 |

For the purpose of assessing the storage stability of the bleaching activators when used in washing agents, perborate was added to a washing agent of conventional composition together with a quantity of activator sufficient to activate 60% to 70% of the perborate within 20 to 30 minutes under normal washing conditions. The well-mixed samples were stored in open glass bottles in an air conditioning cabinet at 30° C. and 75% relative humidity. In addition to the equivalent quantity of activator, each sample contained 5 gm of a washing agent of the following composition (percent by weight):

8.5% n-dodecylbenzenesulfonate (Na salt)
3.5% sodium soap (coconut and tallow fatty acids 1:1)
4.0% fatty alcohol 10-fold ethoxylated ($C_{16-18}$ mixture, iodine number = 50)
40.0% pentasodiumtripolyphosphate
5.0% sodium silicate ($Na_2O:SiO_2$ = 1:3.3)
2.0% mg silicate
1.5% carboxymethylcellulose
0.5% Na ethylenediaminotetraacetate
0.3% optical brightener
7.5% sodium sulfate
20.0% sodium perborate tetrahydrate
7.2% water The perborate and the activator were present in a granulated form having a grain size of between 0.2 to 0.4 mm. All the components were carefully mixed.

Two samples of each activator were analyzed at the commencement of the test and after one and two weeks storage time. The samples were added in their entirety to 1 liter of water and were agitated for 15 minutes at 30° C. 100 ml of the solution were added to 200 gm of ice and 20 ml of acetic acid. 6 ml of a 10% KI solution were added and the mixture was immediately titrated with 0.1 N $Na_2S_2O_3$ with the addition of starch solution. The content of peracid was determined in this manner. 30 ml of 50% $H_2SO_4$, 1 ml of 3% ammonium molybdate solution and 5 ml of 10% KI solution were added to a further 100 ml of the test solution and the mixture was also titrated with 0.1 N $Na_2S_2O_3$ after 5 minutes. The content of peracetic acid and any perborate present is determined on this evaluation.

If the titration values of the non-stored samples are assumed to be 100, one obtains from the values of the stored samples the percentage contents of remaining active oxygen in the sole form of peracid and as the total of perborate + peracid. The values found are listed in the following Table III.

TABLE III

| Acylated Uracil Activators | Active Oxygen | Storage Time 0 | 1 week | 2 weeks |
|---|---|---|---|---|
| I | Peracid | 100 | 90 | 72 |
| | Peracid + perborate | 100 | 95 | 86 |
| II | Peracid | 100 | 50 | 10 |
| | Peracid + perborate | 100 | 65 | 26 |
| III | Peracid | 100 | 67 | 18 |
| | Peracid + perborate | 100 | 83 | 47 |
| IV | Peracid | 100 | 73 | 10 |
| | Peracid + perborate | 100 | 84 | 41 |
| V | Peracid | 100 | 46 | 14 |
| | Peracid + perborate | 100 | 66 | 42 |
| VI | Peracid | 100 | 33 | 2 |
| | Peracid + perborate | 100 | 55 | 30 |
| VII | Peracid | 100 | 51 | 41 |
| | Peracid + perborate | 100 | 92 | 75 |
| Tetra-acetyl-glycoluril | Peracid | 100 | 50 | 14 |
| | Peracid + perborate | 100 | 53 | 31 |

The preceding specific embodiments are illustrative of the invention. It is to be understood, however, that other expedients disclosed herein or known to those skilled in the art, may be employed without departing from the spirit of the invention or the scope of the appended claims.

We claim:

1. The method of activating aqueous solutions of percompounds selected from the group consisting of hydrogen peroxide and water-soluble inorganic peroxyhydrates containing from 20 mg to 500 mg per liter of active oxygen, said solution having a pH of 4 to 12 and a temperature of from 10° C. to 70° C. which consists essentially of adding to said aqueous solution as an activator, an acylated uracil of the formula selected from the group consisting of

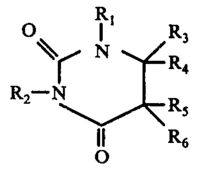

and

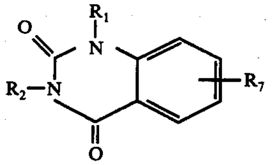

wherein at least one of $R_1$ and $R_2$ is an acyl of an acid selected from the group consisting of alkanoic acids having 2 to 4 carbon atoms and benzoic acid, and the other of $R_1$ or $R_2$ is a member selected from the group consisting of alkanoyl having 2 to 4 carbon atoms, benzoyl, and $R_3$; $R_3$, $R_4$, $R_5$ and $R_6$ are independently members selected from the group consisting of hydrogen, alkyl having 1 to 4 carbon atoms, haloalkyl having 1 to 4 carbon atoms, alkoxyalkyl having 2 to 6 carbon atoms, carboxyalkyl having 2 to 4 carbon atoms, and alkoxycarbalkyl having 3 to 6 carbon atoms, and $R_7$ is a member selected from the group consisting of hydrogen, halogen, alkyl having 1 to 4 carbon atoms, $—CO_2Me$, $—SO_3Me$, amido, cyano, sulfamido and nitro, where Me is an alkali metal or ammonium.

2. The method of claim 1, wherein said aqueous solution has a pH of from 7 to 11.5.

3. The method of claim 2, wherein said aqueous solution has a pH of from 8 to 11.

4. The method of claim 1, wherein said activator is added to said aqueous solution in an amount sufficient that from 0.1 to 2 acyls in said activator are present per active oxygen atom in said aqueous solution.

5. The method of claim 1, wherein from 50 mg to 250 mg per liter of active oxygen are present in said aqueous solution.

6. Solid oxidation compositions for bleaching and washing agents consisting essentially of from 5% to 90% by weight of an acylated uracil of the formula selected from the group consisting of

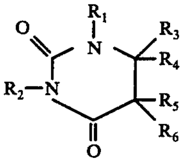

and

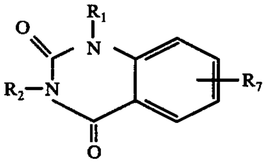

wherein at least one of $R_1$ and $R_2$ is an acyl of an acid selected from the group consisting of alkanoic acids having 2 to 4 carbon atoms and benzoic acid, and the other of $R_1$ or $R_2$ is a member selected from the group consisting of alkanoyl having 2 to 4 carbon atoms, benzoyl, and $R_3$; $R_3$, $R_4$, $R_5$ and $R_6$ are independently members selected from the group consisting of hydrogen, alkyl having 1 to 4 carbon atoms, haloalkyl having 1 to 4 carbon atoms, alkoxyalkyl having 2 to 6 carbon atoms, carboxyalkyl having 2 to 4 carbon atoms, and alkoxycarbalkyl having 3 to 6 carbon atoms, and $R_7$ is a member selected from the group consisting of hydrogen, halogen, alkyl having 1 to 4 carbon atoms, $—CO_2Me$, $—SO_3Me$, amido, cyano, sulfamido and nitro, where Me is an alkali metal or ammonium, as an activator for percompounds, from 95% to 10% by weight of at least one alkaline-reacting builder salt, from 0 to 15% by weight of a surface-active compound selected from the group consisting of anionic surface-active compounds, nonionic surface-active compounds and amphoteric surface-active compounds, and from 0 to 10% by weight of stabilizers for percompounds.

7. The solid oxidation compositions for bleaching and washing agents of claim 6 containing from 7% to 70% by weight of said activator, from 15% to 93% by weight of said builder salt and from 0% to 10% by weight of said surface-active compound.

8. Solid powdery to granular oxidation compositions for bleaching and washing agents consisting essentially of a water-soluble solid inorganic percompound in the form of its alkali metal salt and, as an activator, an acylated uracil of the formula selected from the group consisting of

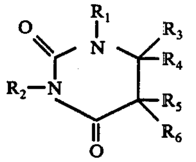

and

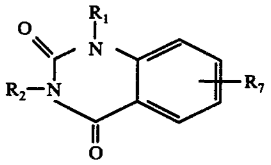

wherein at least one of $R_1$ and $R_2$ is an acyl of an acid selected from the group consisting of alkanoic acids having 2 to 4 carbon atoms and benzoic acid, and the other of $R_1$ or $R_2$ is a member selected from the group consisting of alkanoyl having 2 to 4 carbon atoms, benzoyl, and $R_3$; $R_3$, $R_4$, $R_5$ and $R_6$ are independently members selected from the group consisting of hydrogen, alkyl having 1 to 4 carbon atoms, haloalkyl having 1 to 4 carbon atoms, alkoxyalkyl having 2 to 6 carbon atoms, carboxyalkyl having 2 to 4 carbon atoms, and alkoxycarbalkyl having 3 to 6 carbon atoms, and $R_7$ is a member selected from the group consisting of hydrogen, halogen, alkyl having 1 to 4 carbon atoms, $—CO_2Me$, $—SO_3Me$, amido, cyano, sulfamido and nitro, where Me is an alkali metal or ammonium, said activator being present in an amount sufficient that from 0.05 to 5 acyls in said activator are present per active oxygen atoms in said percompound.

9. The solid, powdery to granular oxidation compositions for bleaching and washing agents of claim 8 wherein from 0.1 to 2 acyls are present per active oxygen atoms in said percompound.

10. The solid, powdery to granular oxidation compositions for bleaching and washing agents of claim 8 wherein 0.5 to 10 mols of peroxygen are present for every 1 mol of monoacylated uracil compound.

11. The solid, powdery to granular oxidation compositions for bleaching and washing agents of claim 8 wherein 1 to 5 mols of peroxygen are present for every 1 mol of monoacylated uracil compound.

12. The solid, powdery to granular oxidation compositions for bleaching and washing agents of claim 8 wherein 1 to 20 mols of peroxygen are present for every 1 mol of diacylated uracil compound.

13. The solid, powdery to granular oxidation compositions for bleaching and washing agents of claim 8 wherein 2 to 10 mols of peroxygen are present for every 1 mol of diacylated uracil compound.

14. The solid, powdery to granular oxidation compositions for bleaching and washing agents of claim 8 wherein said acylated uracil is present in an amount of from 0.5% to 50% by weight.

15. The solid, powdery to granular oxidation compositions for bleaching and washing agents of claim 8 wherein said acylated uracil is present in an amount of from 1% to 30% by weight.

16. The solid, powdery to granular oxidation compositions for bleaching and washing agents of claim 8 wherein at least one of $R_1$ and $R_2$ is acetyl.

17. The solid, powdery to granular oxidation compositions for bleaching and washing agents of claim 8 wherein both $R_1$ and $R_2$ are acetyl.

18. The solid, powdery to granular oxidation compositions for bleaching and washing agents of claim 8 wherein up to 10% by weight of a stabilizer for percompounds is present.

19. Diacylated 5,6-dihydrouracils having the formula

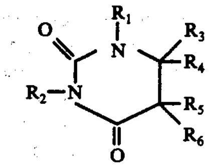

wherein $R_1$ and $R_2$ are acyls of acids selected from the group consisting of alkanoic acids having 2 to 4 carbon atoms and benzoic acid, $R_3$, $R_4$, $R_5$ and $R_6$ are independently members selected from the group consisting of hydrogen, alkyl having 1 to 4 carbon atoms, haloalkyl having 1 to 4 carbon atoms, alkoxyalkyl having 2 to 6 carbon atoms, carboxyalkyl having 2 to 4 carbon atoms, and alkoxycarbalkyl having 3 to 6 carbon atoms.

20. A diacylated 5,6-dihydrouracil of claim 19 being 1,3-diacetyl-5,6-dihydrouracil.

* * * * *